(12) United States Patent
Gleim et al.

(10) Patent No.: US 8,808,159 B2
(45) Date of Patent: Aug. 19, 2014

(54) APPARATUS FOR STIMULATING LOCAL AND HIGHER HOMEOSTATIC AUTOREGULATORY MECHANISMS IN THE ORGANISM

(71) Applicant: Peter Gleim, Triesen (LI)

(72) Inventors: Peter Gleim, Triesen (LI); Rainer Klopp, Wandlitz (DE)

(73) Assignee: Bemer International AG, Triesen (LI)

( * ) Notice: Subject to any disclaimer, the term of this patent is extended or adjusted under 35 U.S.C. 154(b) by 0 days.

(21) Appl. No.: 14/055,626

(22) Filed: Oct. 16, 2013

(65) Prior Publication Data

US 2014/0046116 A1 Feb. 13, 2014

Related U.S. Application Data

(62) Division of application No. 13/391,599, filed as application No. PCT/EP2010/062166 on Aug. 20, 2010, now Pat. No. 8,585,570.

(30) Foreign Application Priority Data

Aug. 25, 2009 (EP) .................................. 09168634

(51) Int. Cl.
*A61N 2/00* (2006.01)
*A61N 2/02* (2006.01)

(52) U.S. Cl.
CPC . *A61N 2/004* (2013.01); *A61N 2/02* (2013.01)
USPC ................................................. 600/14; 600/9

(58) Field of Classification Search
CPC ........................................................ A61N 2/02
USPC .................................. 600/9–15; 128/897–899
See application file for complete search history.

(56) References Cited

U.S. PATENT DOCUMENTS

2008/0125618 A1* 5/2008 Anderson et al. ............... 600/14

FOREIGN PATENT DOCUMENTS

| DE | 10237519 | 4/2003 |
|----|----------|--------|
| WO | 0076582 | 12/2000 |
| WO | 2008025731 | 3/2008 |
| WO | 2008127011 | 10/2008 |
| WO | 2009090440 | 7/2009 |

* cited by examiner

*Primary Examiner* — Christine Matthews
*Assistant Examiner* — Joshua D Lannu
(74) *Attorney, Agent, or Firm* — Duane Morris LLP; J. Rodman Steele, Jr.; Gregory M. Lefkowitz

(57) ABSTRACT

The invention relates to an apparatus for stimulating local and higher homeostatic autoregulatory mechanisms during the sleep phase and the rest of relaxation phase of the organism by means of a pulsed electromagnetic field. Said apparatus comprises a pulse generator, a control device, and a filed generating device. The pulse generator is designed in such a way as to generate a pulsed electromagnetic field along with the control device and the filed generating device by applying 5 special series of pulses in which the frequency is the same for all signals, ranging from 8 to 15 Hz, the series of pulses are repeated multiple times, and the control time amounts to at least 3.5 h within a period of 7 to 9 hours.

3 Claims, 4 Drawing Sheets nWBC/A (changes in %)

$Q_L$ (changes in %)

APPARATUS FOR STIMULATING LOCAL AND HIGHER HOMEOSTATIC AUTOREGULATORY MECHANISMS IN THE ORGANISM

CROSS-REFERENCE TO RELATED APPLICATIONS

This application is a divisional of U.S. Utility application Ser. No. 13/391,599 filed Apr. 2, 2012, which is a §371 International Application No. PCT/EP2010/062166, filed Aug. 20, 2010, which claims priority to European Application No. EP 09168634.5, filed Aug. 25, 2009, the entire contents of which are incorporated herein by reference.

BACKGROUND OF THE INVENTION

The invention relates to an apparatus for stimulating local and higher homeostatic autoregulatory mechanisms during the sleep phase and the rest or relaxation phase of the organism on the basis of a pulsed electromagnetic field.

It is already known to influence the microcirculation by means of electromagnetic pulses.

EP 0 995 463 discloses an apparatus which is used to influence biological processes in the human body by means of pulsed electromagnetic fields, in particular in order to increase $O_2$ utilization and to stimulate metabolic processes. The individual pulses can follow a function represented by a formula.

WO 2008/025731 describes an apparatus for generating a pulsed electromagnetic field including periodic pulses with rising and falling envelope curves in accordance with defined measurement data of the microcirculation of the blood.

SUMMARY OF THE INVENTION

The object of the invention is to provide an apparatus which serves to achieve increased regeneration and restitution effects in the microcirculatory system during the sleep phase and the relaxation phase of the organism, taking into account the reduced heart minute volume in the sleep or relaxation phase. This concerns functional improvements in the microcirculation as well as the lymphatic flow and, above all, the immune system.

According to the invention, the apparatus comprises a pulse generator, a control device and a field generation device which interact to generate a pulsed electromagnetic field, wherein pulse sequences with defined levels, defined intervals and defined frequencies influence the pulsation of the field. In this way, effects stimulating homeostatic autoregulatory mechanisms in the organism can be produced.

When considering which morphological and functional system of the organism allows representative statements about the relevant therapeutic effects of a treatment method to be made, outstanding importance is to be attributed to the blood as a transport organ. The biological function of the blood as an organ consists mainly in its contributions to homeostasis, i.e. to the maintenance of a constant "internal environment" due to the interaction of various control and regulatory processes in order to achieve steady states, and in its contribution to immune responses.

The most important "constant features" of the organism under physiological conditions are:
water content
composition of the body fluids. Blood constants: e.g. pH=7.3, content of mineral ions (sodium, potassium, magnesium, iron, chloride, phosphate, hydrogencarbonate, protein content), the glucose concentrations are also adjusted to a level with little variation. Maintenance of the blood volume (trans-capillary fluid exchange, stop of bleeding, clotting)
body temperature of the (systemic) mean arterial blood pressure.

The living organism is a multi-stable system in which various morphological units are functionally linked by the blood as an organ in order to ensure homeostasis. These units are the external respiration and metabolism including the cardiopulmonary circulation and the kidney function including blood pressure regulation.

During the complex interaction of control and regulatory processes in the organism in order to maintain homeostasis, all parts of the organism are linked to each other in such a manner that changes in a subsystem (tissue, organ, organ system) have an effect on other subsystems, causing them to achieve a new steady state, wherein the subsystems are coupled to each other by the nerves and by means of the blood circulation, inter alia by the microcirculation.

The functional state of an organ is substantially dependent on the functional state of its microcirculation. It is generally accepted today that most functional disorders or diseases of the organs are at least determined in their development, or even caused, by microcirculatory disorders. Microcirculatory disorders often develop as a consequence of macrocirculatory disorders and can gradually develop their own dynamics which has a major effect on, or even dominates, the development of the disease, regardless of macrocirculatory processes. Without adequate contribution of the microcirculation, i.e. the transport processes through the microvessels, functional improvements, healing or restitution processes or regeneration processes in the organs are not possible. If the microcirculation is impaired, the symptoms of disorders or diseases can at best be influenced temporarily and to a minor extent, if at all.

The morphological and functional system of the microcirculation is therefore a particularly good indicator of relevant therapeutic and prophylactic effects.

The apparatus according to the invention is intended, above all, to cause defined effects in the microcirculatory system of the blood and to make them visible and verifiable by means of scientifically proven measuring methods and measurement criteria.

The apparatus according to the invention, which comprises a pulse generator, a control device and a field generation device, is characterized in that the pulse generator is designed to interact with the control device and the field generation device so as to generate a pulsed electromagnetic field by emitting pulse sequences, wherein a pulse sequence includes the sequences 1 to 5:
Sequence 1: 0 µT for 1-3 seconds,
Sequence 2: 3-12 µT base signal for 12-16 seconds,
Sequence 3: 30-150 µT additional signal for 100-200 milliseconds,
Sequence 4: sequences 2 and 3 are repeated 8 to 10 times,
Sequence 5: 0 µT for 1-3 seconds
providing that
(1) the frequencies of the base signal and the additional signal are identical, ranging from 8 to 15 Hz;
(2) the pulse sequences are configured to be repeated multiple times, and the control time of all pulse sequences that are repeated multiple times amounts to at least 3.5 hours within a period of 7-9 hours;
(3) the amplitudes of the individual pulses follow an exponential function or rising and falling envelope curves with a harmonic or anharmonic pattern.

The base signal can be interrupted by 3 to 8 breaks of 1 to 3 seconds at 0 µT, thus being shorter.

The control time can be selected to amount to up to 8 hours and in such a manner that pulse sequences are allowed to be repeated multiple times during all of this time. In another embodiment of the invention, the control time can also be selected in such a manner that it allows pulse sequences only for 2 hours and another 2 hours following a 4-hour break without signals (0 µT). In another embodiment of the invention, the control time can also be selected in such a manner that it allows pulse sequences at intervals of 20 to 40 minutes, with adequate breaks without signals (0 µT) in between.

The field generation device is a large coil mat for whole-body treatment, the dimensions preferably being 60-80 cm×150-190 cm. In such a coil mat, multiple individual electromagnetic coils can be distributed evenly or unevenly throughout the entire surface area of the mat in order to produce a flat magnetic field. Depending on the size of the mat, said mat can also contain only a single coil.

The individual coils are advantageously designed as conductor loops with an identical surface area or as conductor loops with different surface areas or as a combination of both variants.

For the purpose of the invention, the term "base signal" means that the maxima of the individual oscillations within the predefined time unit are essentially the same and do not exceed the predefined intensity value, i.e. for example are not greater than 12 µT, preferably not greater than 10 µT, in particular not greater than 4-7 µT.

The base signal consists of a sequence of individual pulses with a pulse width of approx. 33 ms at the aforementioned level of 3-15 µT, for example of 6.5 µT, for the predefined period of 12-16 s. This is followed by an additional pulse with a pulse width of 100-200 ms with an intensity (intensity=pulse strength=electromagnetic flux density) of 30-120 µT, for example of 70 µT.

For the purpose of the invention, the term "additional signal" means therefore that, at a defined time and for a very short period of time, here 100-200 ms, a clearly stronger signal with an intensity exceeding the base signal by at least 18 µT is additionally emitted, wherein the additional signal is superimposed on the base signal for said short period of time. The intensity of the additional signal is preferably 50-110 µT, in particular 60-100 µT.

The pulse sequences consist of individual pulses whose amplitudes follow e.g. an exponential function. A preferred exponential function is described in EP 995463 B1 as $y=x^3 \cdot e^{sin(x^3)}$, wherein the formula indicates the pattern traced by the amplitude y over the time x. The shape of the individual pulses is then approximately the same as shown in FIG. 2 of EP 995463 B1. The individual pulses can also have non-exponential shapes, being rising and falling envelope curves representing harmonic or anharmonic oscillations, as in WO 2008/025731. Alternating pulse groups representing such oscillations are illustrated e.g. in FIGS. 4c to 4f of WO 2008/025731. As a whole, the pulse sequences consist of combined oscillations with an arcuate shape.

Pulses or pulse groups with a stepped or square shape are not a subject-matter of the invention.

Pulse groups with individual pulses whose amplitude corresponds to an e function are preferred for the present invention.

A "multiple repetition" of the pulse sequences means a repetition for 110-240 times, in accordance with the control time.

The electromagnetic field produced influences, advantageously by means of the frequency, the level of the base signal, the level and length of the additional signal and the frequency with which the pulse sequences are repeated, functional features of the body's own regulation of the organism—selected from microcirculatory functional features, macrocirculatory functional features and immunological functional features.

The microcirculatory functional features include
the number of nodal points perfused with blood cells (nNP)
the changes in the venular flow rate ($\Delta Q_{ven}$)
the changes in venular oxygen utilization ($\Delta pO_2$)
the arteriolar or venular vasomotor state ($A_{VM}$)
the number of white blood cells adhering to a defined inner venular wall, nWBC/A.

Further features include
the lactate removal, cLac (e.g. in the skeleton muscles)
the flow rate in the initial lymph vessels, QL
the ejection fraction of the left ventricle, EF
the excretory function of the kidneys during sleep and/or relaxation.

The latter includes e.g. substances to be eliminated with the urine, the pH value and osmolality of the urine and others.

With regard to the microcirculatory functional features, the number of nodal points that are currently perfused with blood cells in a defined microvascular network, nNP, is determined taking into account the number of blood-cell perfused branching points in said network as an indicator of the distribution of the blood. The flow velocity limit of the red blood cells is defined to be $v_{RBC}$=80 µm/s. The evaluation is done in + or − (compared to the defined initial value n=60).

By means of the present invention, using the pulse sequence according to the invention and repeating it for 8 hours, the nNP value is for example increased by 10-15%, compared to the initial value.

The venular flow rate, $Q_{ven}$, and the arteriolar flow rate, $Q_{art}$, define the particle flow (blood cell flow) in defined venules or arterioles. It is given in µm³/s. $\Delta Q_{ven}$ is the change in the venular flow rate and can also be given as a percent change relative to the initial value.

The venular oxygen utilization, $\Delta pO_2$, is given as a percent change relative to the initial value at the time t=0. The absolute difference of the oxygen saturation of the haemoglobin in the arterioles supplying blood and the venules carrying blood away in a network of a selected tissue target is determined. The targets selected are tissue portions of the skin or intestine which comprise large, much branched blood vessel networks representing the circulatory system of the organism and which also belong to the immunologically active organs and are furthermore easy to access for non-invasive measurements.

By means of the present invention, using a pulse sequence in accordance with the invention and repeating it for 8 hours, the $\Delta pO_2$ value is for example increased by 8-10%.

The spontaneous arteriolar (or venular) vasomotor state, $A_{VM}$, is determined by determining the distance-time chart of the autorhythmic contraction movements of smooth muscle cells of the arteriolar vessel wall (measurement of the distance made perpendicular to the longitudinal axis of the microvessel from the endothelium surface to the opposite endothelium surface at equidistant measuring times; 60 measured values per second; determination of the combined oscillation; FOURIER analysis; determination of the amplitude-frequency spectrum). The criterion is the surface area, A, below the envelope of the amplitude-frequency spectrum of the arteriolar vasomotion (a combined oscillation). The value is given as a percent change relative to the initial values.

The number of white blood cells adhering to a defined inner venular wall, nWBC/A, is measured on the defined inner surface of the venule of A=18000 μm². All white blood cells adhering to the endothelium for more than 20 seconds are counted.

By means of the present invention, using a pulse sequence in accordance with the invention and repeating it for 8 hours, the nWBC/A value is increased for example by 12%. The comparative value is less than 4%.

The stimulatory effects caused by the apparatus according to the invention and the amplitude-modulated and frequency-modulated pulsed electromagnetic field produced by means of said apparatus concern local regulatory mechanisms of the microcirculation of the blood, such as the spontaneous arteriolar vasomotion, wherein particular preference is given to immunologically active organs, such as the skin and intestine, and in this connection the tonus regulation of smallest microvessels by means of their own muscles and initiated by the endothelium.

With regard to the effect on local regulatory mechanisms, it has been found that the apparatus according to the invention with the pulsed electromagnetic field generated, including the very special pulse sequence, pulse level and pulse duration, serves to achieve more significant feature changes, compared to known electromagnetic fields, in particular feature changes that are 9-20% higher.

This is particularly surprising in light of the fact that pulses including a base signal and an additional signal in higher frequency ranges do not show these results.

A particular advantage of the invention is that the pulse sequences can be repeated multiple times during several hours at night while the patient is asleep, thus not necessarily involving additional effort.

Moreover, the invention provides prophylactic and complementary therapeutic effects concerning many processes of homeostatic regulation of the whole organism, e.g. the excretory function of the kidneys during night sleep.

The invention also relates to the provision of a prophylactic or therapeutic method for stimulating local and higher homeostatic autoregulatory mechanisms during the sleep phase and the rest/relaxation phase of the organism, characterized in that the body or a part of the body of a patient is exposed to a pulsed electromagnetic field, wherein a pulse sequence includes the sequences 1 to 5:
Sequence 1: 0 μT for 1-3 seconds,
Sequence 2: 3-12 μT base signal for 12-16 seconds,
Sequence 3: 30-150 μT additional signal for 100-200 milliseconds,
Sequence 4: sequences 2 and 3 are repeated 8 to 10 times,
Sequence 5: 0 μT for 1-3 seconds
providing that
    the frequencies of the base signal and the additional signal are identical, ranging from 8 to 15 Hz;
    the pulse sequences are configured to be repeated multiple times, and the control time of all pulse sequences that are repeated multiple times amounts to at least 3.5 hours within a period of 7-9 hours;
    the amplitudes of the individual pulses follow an exponential function or rising and falling envelope curves with a harmonic or anharmonic pattern.

The duration of treatment ranges from a one-off treatment to a daily treatment for 2 to 90 days, wherein interruptions of 2-5 days can be planned.

If treatment is done for 7 to 9 hours during the sleep phase of a patient, the pulse sequence according to the invention can be emitted continuously within this period of time. Another advantageous embodiment consists in a 2-hour pulse sequence, a 4-hour break and another 2-hour pulse sequence. Another advantageous embodiment consists in pulse sequences lasting half an hour and half-hour breaks in between for a total of 7-9 hours.

An advantageous overall control time of the pulse sequences is 8 hours. This and other advantageous embodiments can be planned in accordance with the age, constitution, fitness and condition of the individual to be treated.

The invention also relates to the use of an apparatus for stimulating local and higher homeostatic mechanisms during the sleep phase and the rest or relaxation phase of the organism, comprising a pulse generator and a field generation device, wherein the pulse generator is designed to interact with the field generation device so as to generate a pulsed electromagnetic field by emitting pulse sequences, wherein a pulse sequence includes the sequences 1 to 5:
Sequence 1: 0 μT for 1-3 seconds,
Sequence 2: 3-12 μT base signal for 12-16 seconds,
Sequence 3: 30-150 μT additional signal for 100-200 milliseconds,
Sequence 4: sequences 2 and 3 are repeated 8 to 10 times,
Sequence 5: 0 μT for 1-3 seconds
providing that
    the frequencies of the base signal and the additional signal are identical, ranging from 8 to 15 Hz;
    the pulse sequences are configured to be repeated multiple times, and the control time of all pulse sequences that are repeated multiple times amounts to at least 3.5 hours within a period of 7-9 hours;
    the amplitudes of the individual pulses follow an exponential function or rising and falling envelope curves with a harmonic or anharmonic and generally arcuate pattern.

BRIEF DESCRIPTION OF THE DRAWINGS

The invention will now be explained by means of examples. In the appended drawing.

DETAILED DESCRIPTION

Example 1

The apparatus consists of a pulse generator which is supplied with a mains voltage of 230 V/50 Hz (alternating current), a control device for different field strengths on the applicators and a coil mat as an applicator. The operating voltage of the control device, and hence the nominal power on the coil mat, is max. 12 V (direct current). A preferred apparatus is the BEMER apparatus of Innomed International AG, Liechtenstein. The coil mat has a surface area of 70×170 cm, so as to accommodate the whole or almost the whole body of a patient who is lying down. Three coil pairs are distributed in the coil mat. The electromagnetic flux density of the electromagnetic field and the time intervals are controlled in a series of stages by means of the control device.

The apparatus including the pulse generator designed according to the invention is tested in a group of test persons.

Number of test persons: 24, divided into a verum group of 12 test persons and a control group of 12 test persons. The test persons were male, aged 44-55 years, exposed to stress, had sleep disorders (difficulty in falling asleep and maintaining sleep), clinically NAD.

The verum group was treated as follows:
lying down on the coil mat
pulse sequence (combined oscillations with an arcuate shape)

| Sequence 1 | 0 µT | 2 s | |
| Sequence 2 | 6.5 µT | 15 s | 10 Hz |
| Sequence 3 | 80 µT | 120 ms | 10 Hz |
| Sequence 4 | sequences 2 and 3 are repeated eight times | | |
| Sequence 5 | 0 µT | 2 s | |

The base signal included 4 breaks of one second each.
Repetition of the pulse sequence for a total of 8 hours of treatment
Measurement of the features from time 0 to 8 hours every 2 hours (equidistant)
The control group was treated as follows:
lying down on the coil mat
pulse sequence: none (placebo)
measurement as in verum group.

Figure 1:
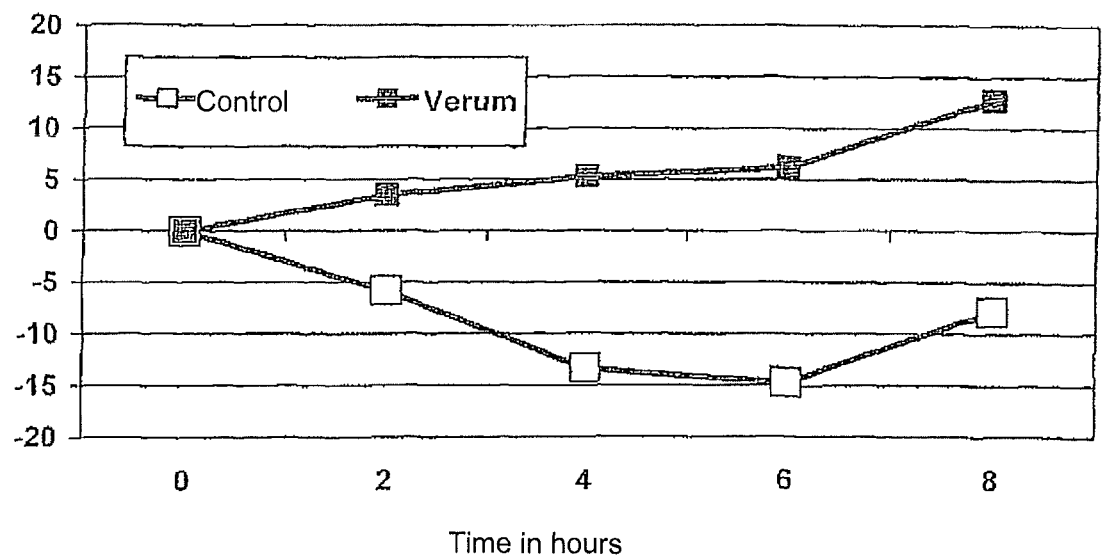
FIG. 1 shows a diagram relating to the nNP feature in the target tissues, i.e. subcutaneous tissue, intestine, following the use of the apparatus according to the invention.

Treatment was done on three successive days in both groups. The measuring methods used were intravital microscopy, Laser DOPPLER microflow measurement, white-light spectroscopy, intravital microscopic reflection spectroscopy and clinical laboratory diagnostics. The features selected from the features examined were:

1. Number of nodal points perfused with blood cells, nNP, in a defined tissue unit ($V=2000$ µm$^3$) in the target tissues, i.e. subcutaneous tissue, intestine As can be seen in the illustration in FIG. 1, the verum group, unlike the control group, showed an almost continuous increase during the treatment, achieving a change of 13%. In contrast, the value of the control group decreased to −15% and only increased to −8% in the last two hours.

Figure 2:
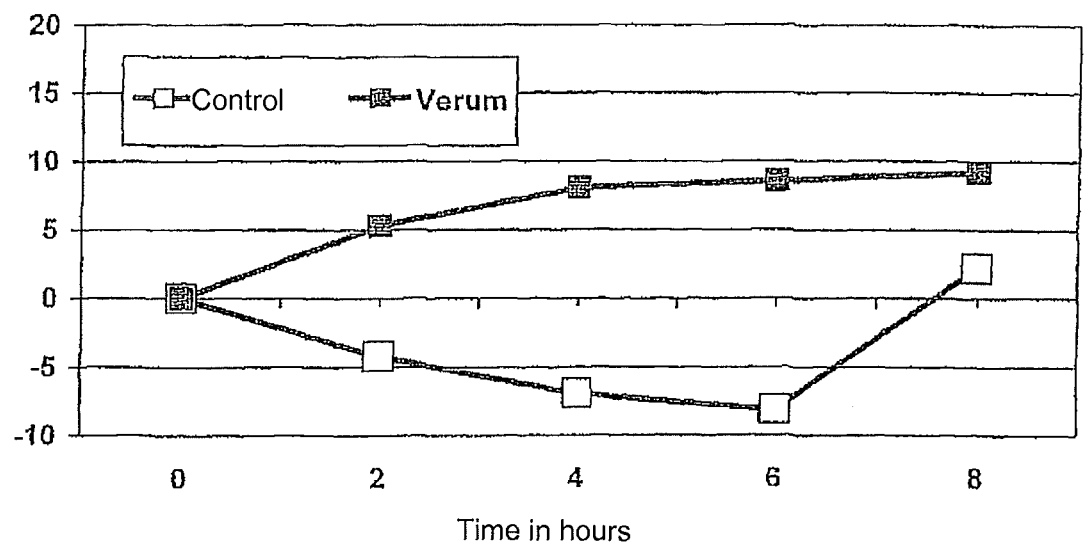
FIG. 2 shows a diagram relating to the $\Delta pO_2$ feature in the target tissue, i.e. intestine, following the use of the apparatus according to the invention.

2. Venular oxygen utilization, $\Delta pO_2$, in the microcirculation of a defined tissue volume unit ($V=2000$ µm$^3$) in the target tissue, i.e. intestine As can be seen in the illustration in FIG. 2, the verum group showed an increase by max. 9%, to in contrast to the control group. In the control group, there was no overall change, but a temporary decrease to −8% after 6 hours.

Figure 3:
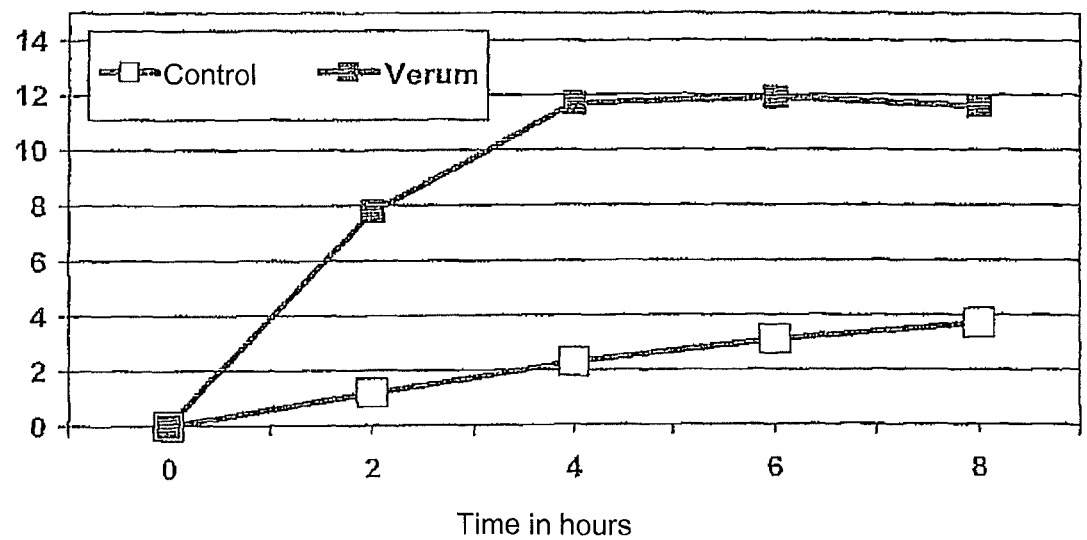
FIG. 3 shows a diagram relating to the nWBC/A feature in the target tissues, i.e. subcutaneous tissue, intestine, following the use of the apparatus according to the invention.
Figure 4:
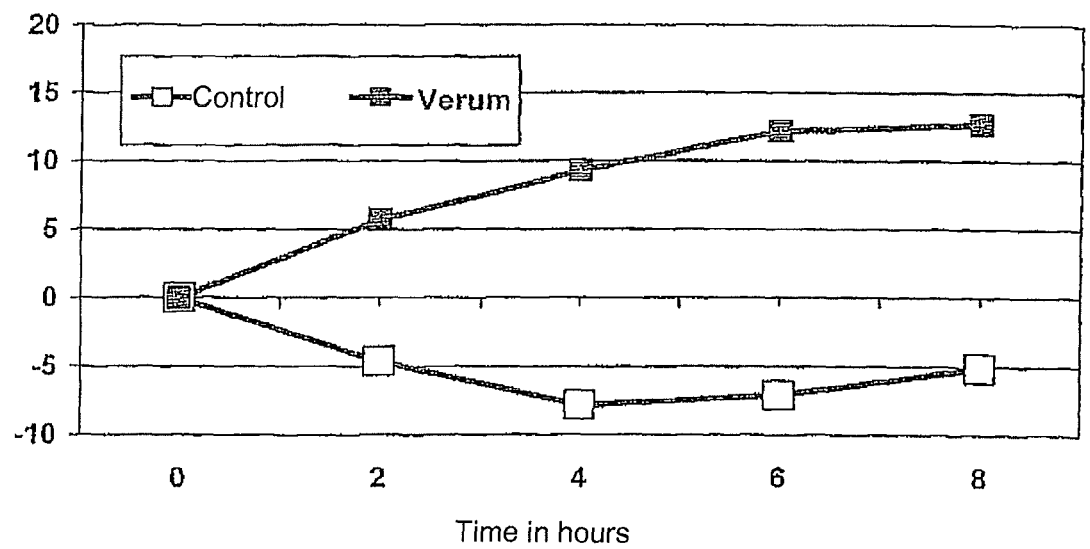
FIG. 4 shows a diagram relating to the feature of flow rate in the initial lymph vessels, QL, in the target tissues, i.e. subcutaneous tissue, intestine, following the use of the apparatus according to the invention.
Figure 5:
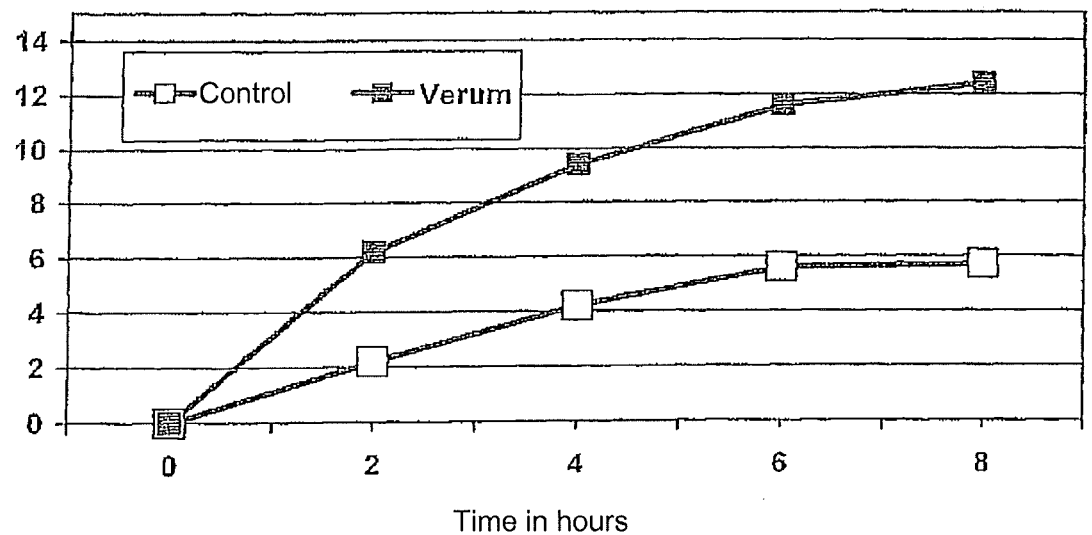
FIG. 5 shows a diagram relating to the feature of lactate removal, cLac, in the target tissue, i.e. the skeleton muscles, following the use of the apparatus according to the invention.
Figure 6:
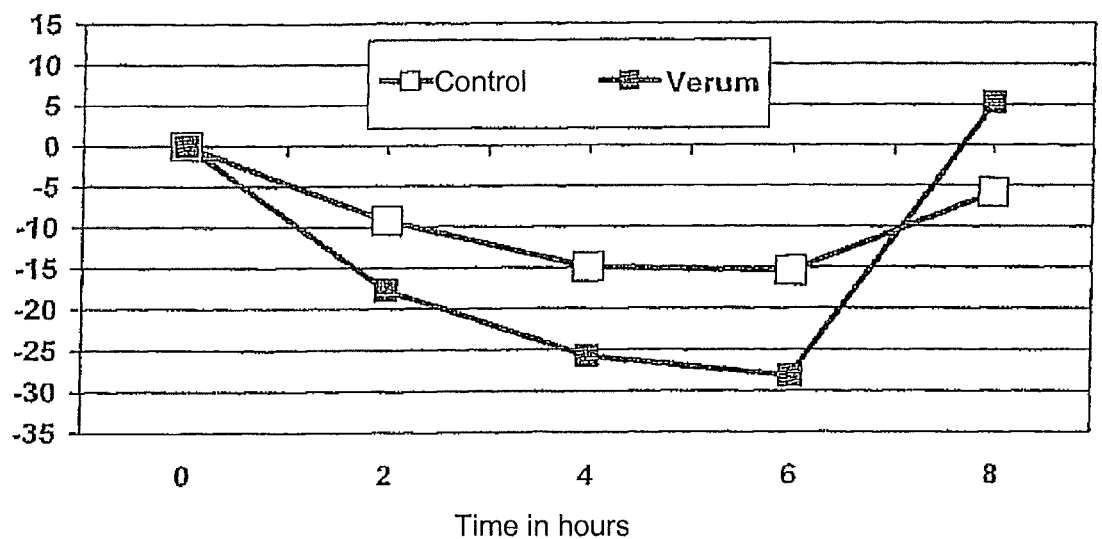
FIG. 6 shows a diagram relating to the feature of the ejection fraction of the left ventricle, EF, following the use of the apparatus according to the invention.
Figure 7:
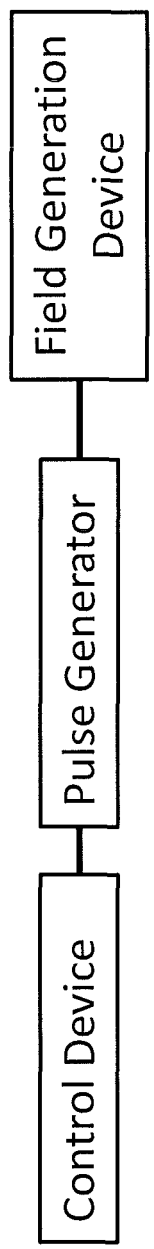
FIG. 7 shows a diagram of an apparatus as described herein.

3. Number of white blood cells adhering to a defined inner venular wall, nWBC/A, in the microcirculation of a defined tissue volume unit ($V=2000$ µm$^3$) in the target tissue, i.e. intestine As can be seen in the illustration in FIG. 3, the verum group showed a significantly increased change of more than 11% 8 hours after treatment, in contrast to the control group. The value achieved by the control group was only slightly below 4%.

4. Flow rate in the initial lymph vessels, QL, in the target tissue, i.e. subcutaneous tissue, intestine While the control group showed a decrease by −5%, and temporarily even more, the verum group was able to achieve an increase of 13%.

5. Lactate ebbing, cLac, in the target tissue, i.e. skeleton muscles

In contrast to an increase in the control group by approx. 5%, the verum group showed increases of more than 12% for this feature.

6. Ejection fraction of the left ventricle, EF

Following a decrease by more than −15%, the control group achieved a final value of approx. −7% after 8 hours. The changes were much more pronounced in the verum group, which showed a decrease of almost −30% after 6 hours, but achieved a value of +5% after 8 hours.

Overall, the apparatus according to the invention serves to achieve significant changes concerning features of the microcirculation of the blood as well as other features, i.e. kidney function (increased excretion of substances to be eliminated with the urine), stimulated immune response in the skin and intestine during night sleep. The values are 9-20% higher than expected.

Example 2

Comparative Example

The apparatus of the present invention is compared with the apparatus according to WO 2008/25731.
An apparatus and a coil mat as in Example 1 are used.
Test persons: male, aged 45-55 years, as part of a physical therapy and fitness scheme.
Verum group: 12 test persons, comparative group: 12 test persons, selected by means of a random generator.
Treatment interval: 30 days (treatments done blindfolded), measuring interval: also 30 days (equidistant and at the same time of day).
(a) Treatment of the verum group, lying down on the coil mat and with the pulse sequence (combined oscillations with an arcuate shape) in each case:

| Sequence 1 | 0 µT | 2 s | | |
| Sequence 2 | 8 µT | 12 s | 12 Hz | (base signal) |
| Sequence 3 | 100 µT | 150 ms | 12 Hz | |
| Sequence 4 | sequences 2 and 3 are repeated eight times | | | |
| Sequence 5 | 0 µT | 2 s | | |

The base signal included 3 breaks of 1 s each. The aforesaid pulse sequence 1-5 is repeated for a total of 7 hours. Measurements are taken on days 0, 5, 10, 15, 20, 25 and 30.

(b) Treatment of the comparative group, lying down on the coil mat and with the pulse sequence according to WO 2008/025731 (combined oscillations with an arcuate shape) in each case:
Base pulse: 60 µT, pulse width: 30 ms
Additional pulse: 180 µT, pulse width: 150 ms
Frequency of the additional pulse: 3 per minute
Overall frequency: 30 Hz
Duration of treatment: 2×25 minutes with a 2 h break in between
Frequency and continuation of treatment: daily for 30 days
Measurements on days 0, 5, 10, 15, 20, 25, 30

(c) Evaluation methods
Vital microscopic examination unit with computer-based image processing (KONTRON system), vital microscopic reflection spectrometry (SPEX system), combined Laser Doppler microflow measurement and white-light spectroscopy (LEA system).

(d) Features used for evaluation

Features:
spontaneous arteriolar vasomotion, AVM (surface area below the envelope of the originary amplitude-frequency spectrum of the small-calibre arteriolar vasomotion),
number of nodal points that are currently perfused with blood cells in the defined capillary network, nNP,
venular oxygen utilization, $\Delta pO_2$,
flow rate in the initial lymph vessels, QL.

Target tissue: intestine (muscle layer of the rectum)

Biometry:

WILCOXON rank-sum test ($\alpha=5\%$)

TABLE 1

Spontaneous arteriolar vasomotion, AVM

| | Change in % by days | | | | | |
|---|---|---|---|---|---|---|
| | 0 | 5 | 10 | 15 | 20 | 25 | 30 |
| Comparative example 2(a) INVENTION | — | 18.3 | 25.1 | 28.3 | 29.9 | 30.3 | 30.6 |
| Comparative example 2(b) WO2008/025,731 | — | 6.2 | 14.6 | 15.2 | 15.5 | 15.6 | 15.6 |

TABLE 2

Number of nodal points perfused with blood cells, nNP

| | Change in % by days | | | | | |
|---|---|---|---|---|---|---|
| | 0 | 5 | 10 | 15 | 20 | 25 | 30 |
| Comparative example 2(a) INVENTION | — | 15.1 | 22.3 | 27.0 | 31.8 | 33.5 | 34.9 |
| Comparative example 2(b) | — | 4.9 | 9.6 | 13.9 | 15.2 | 15.6 | 15.7 |

TABLE 3

Venular oxygen utilization, $\Delta pO_2$

| | Change in % by days | | | | | |
|---|---|---|---|---|---|---|
| | 0 | 5 | 10 | 15 | 20 | 25 | 30 |
| Comparative example 2(a) INVENTION | — | 15.1 | 25.2 | 30.6 | 35.0 | 36.6 | 37.9 |
| Comparative example 2(b) WO2008/025,731 | — | 5.0 | 8.8 | 14.4 | 15.8 | 18.1 | 18.3 |

TABLE 4

Flow rate in the initial lymph vessels, QL

| | Change in % by days | | | | | |
|---|---|---|---|---|---|---|
| | 0 | 5 | 10 | 15 | 20 | 25 | 30 |
| Comparative example 2(a) INVENTION | — | 20.8 | 29.2 | 34.8 | 40.4 | 42.0 | 44.2 |
| Comparative example 2(b) WO2008/025,731 | — | 4.5 | 7.9 | 9.9 | 11.6 | 14.8 | 15.2 |

The comparison shows significant differences between the state-of-the-art apparatus according to WO 2008/025731 and the invention for all four measured features of the microcirculation of the blood. The QL feature is partly 3 to 4 times higher, other features 1.5 to 2 times.

What is claimed:

1. An apparatus for stimulating local and higher homeostatic autoregulatory mechanisms in an organism, comprising a pulse generator, a control device, a field generation device, and a non-transitory computer readable storage medium comprising non-transitory instructions configured to cause the pulse generator to generate a pulsed electromagnetic field by emitting a pulse sequence that includes sequences 1 to 5:
Sequence 1: 0 µT for 1-3 seconds,
Sequence 2: 3-12 µT base signal for 12-16 seconds,
Sequence 3: 30-150 µT additional signal for 100-200 milliseconds,
Sequence 4: sequences 2 and 3 are repeated 8 to 10 times,
Sequence 5: 0 µT for 1-3 seconds
providing that
frequencies of the base signal and the additional signal are identical, ranging from 8 to 15 Hz;
the pulse sequences are configured to be repeated multiple times, and a control time of all pulse sequences that are repeated multiple times amounts to at least 3.5 hours within a period of 7-9 hours;
amplitudes of individual pulses follow an exponential function or arcuate, rising and falling envelope curves with a harmonic or anharmonic pattern.

2. An apparatus according to claim 1, wherein in said pulse sequence, the base signal includes 3-8 breaks of 1-3 seconds at 0 µT.

3. An apparatus according to claim 1, wherein in the pulsed electromagnetic field generated, a level of the base signal, a level of the additional signal and a frequency with which the pulse sequences are repeated are controlled in accordance with available values selected from:
a number of nodal points perfused with blood cells (nNP),
changes in a venular flow rate ($\Delta Q$),
changes in venular oxygen utilization ($\Delta pO_2$),
an arteriolar or venular vasomotor state ($A_{VM}$),
a number of white blood cells adhering to a defined inner venular wall (nWBC/A),
a lactate removal rate (cLac),
a flow rate in an initial lymph vessel (QL),
an ejection fraction of the left ventricle (EF), and
an excretory function of kidneys during sleep and/or relaxation.

* * * * *